United States Patent
Hong et al.

(10) Patent No.: US 12,285,524 B2
(45) Date of Patent: Apr. 29, 2025

(54) SUSTAINED-RELEASE PHARMACEUTICAL COMPOSITIONS COMPRISING AN ANTIPSYCHOTIC DRUG AND USES THEREOF

(71) Applicants: TAIWAN LIPOSOME CO., LTD., Taipei (TW); TLC BIOPHARMACEUTICALS, INC., South San Francisco, CA (US)

(72) Inventors: Keelung Hong, South San Francisco, CA (US); Jonathan Fang, South San Francisco, CA (US); Hao-Wen Kao, South San Francisco, CA (US); Yi-Yu Lin, South San Francisco, CA (US); Walter Gwathney, South San Francisco, CA (US)

(73) Assignees: TAIWAN LIPOSOME CO., LTD., Taipei (TW); TLC BIOPHARMACEUTICALS, INC., South San Francisco, CA (US)

( * ) Notice: Subject to any disclaimer, the term of this patent is extended or adjusted under 35 U.S.C. 154(b) by 642 days.

(21) Appl. No.: 17/266,201

(22) PCT Filed: Jul. 31, 2019

(86) PCT No.: PCT/US2019/044318
§ 371 (c)(1),
(2) Date: Feb. 5, 2021

(87) PCT Pub. No.: WO2020/033195
PCT Pub. Date: Feb. 13, 2020

(65) Prior Publication Data
US 2021/0308051 A1  Oct. 7, 2021

Related U.S. Application Data

(60) Provisional application No. 62/715,979, filed on Aug. 8, 2018.

(51) Int. Cl.
| A61K 9/1271 | (2025.01) |
| A61K 9/00 | (2006.01) |
| A61K 31/519 | (2006.01) |
| A61K 31/551 | (2006.01) |

(52) U.S. Cl.
CPC .......... *A61K 9/1271* (2013.01); *A61K 9/0019* (2013.01); *A61K 31/519* (2013.01); *A61K 31/551* (2013.01)

(58) Field of Classification Search
None
See application file for complete search history.

(56) References Cited

U.S. PATENT DOCUMENTS

| 2008/0031935 | A1 | 2/2008 | Bodenteich et al. |
| 2012/0171283 | A1* | 7/2012 | Hong ............. A61K 47/28 |
| | | | 514/283 |
| 2013/0202686 | A1 | 8/2013 | Yamashita et al. |
| 2013/0309297 | A1 | 11/2013 | Yamashita et al. |
| 2015/0343063 | A1 | 12/2015 | Helson et al. |
| 2017/0266295 | A1 | 9/2017 | Kan et al. |

FOREIGN PATENT DOCUMENTS

| CN | 1980637 | A | * | 6/2007 | .......... A61K 31/337 |
| CN | 101601654 | A | | 12/2009 | |
| CN | 102406606 | B | | 1/2013 | |
| CN | 108354904 | A | | 8/2018 | |
| WO | 2014121235 | A2 | | 8/2014 | |
| WO | WO-2014121211 | A2 | * | 8/2014 | .......... A61K 31/4196 |
| WO | 2016022549 | A1 | | 2/2016 | |
| WO | 2020023445 | A1 | | 1/2020 | |
| WO | 2020028475 | A1 | | 2/2020 | |

OTHER PUBLICATIONS

Office Action for related China Application No. 201980052433.2, mailed Jun. 15, 2022.
Office Action for related Europe Application No. 19847523.8, mailed Apr. 5, 2022.
Anonymous: "Cerenia for Pets 101: Understanding Side Effects—Innovet Pet" Dec. 20, 2018 Retrieved from Internet: URL:https://www.innovetpet.com/blogs/medications/cerenia-for-dogs [retrieved on Mar. 23, 2022].
Luciano Roman-Albasini et al., "Antidepressant-relevant behavioral and synaptic molecular effects of long-term fasudil treatment in chronically stressed male rats," Neurobiology of Stress, Nov. 1, 2020, pp. 10,0234-10,0234, No. 13.
Pratik Upadhyay et al., "Comparative study between simple and optimized liposomal dispersion of quetiapine fumarate for diffusion through nasal route," Drug Delivery, May 3, 2016, pp. 1,214-1,221, vol. 23, No. 4.
International Search Report & Written Opinion for PCT/US2019/044318, mailed Oct. 16, 2019.
Office Action for related Taiwan application, mailed May 15, 2020.
Office Action for related Taiwan application, mailed Sep. 14, 2020.
Office action for China Application No. 201980052433.2, mailed Jan. 20, 2023.
Office Action for Taiwan Application No. 108127979, mailed Apr. 18, 2022.

* cited by examiner

*Primary Examiner* — Robert A Wax
*Assistant Examiner* — Andre Mach
(74) *Attorney, Agent, or Firm* — Piloff Passino & Cosenza LLP; Rachel Piloff; Sean Passino

(57) ABSTRACT

The present invention relates to a pharmaceutical composition comprising at least one liposome and an antipsychotic drug with a high drug to lipid ratio and encapsulation efficiency. The pharmaceutical composition improves the pharmacokinetic profile and sustains the release of the antipsychotic drug. Also provided is the method for treating schizophrenia or bipolar disorder using the pharmaceutical composition disclosed herein.

14 Claims, 2 Drawing Sheets

SUSTAINED-RELEASE PHARMACEUTICAL COMPOSITIONS COMPRISING AN ANTIPSYCHOTIC DRUG AND USES THEREOF

CROSS-REFERENCE TO RELATED APPLICATION

This application claims the benefit of U.S. Application No. 62/715,979, filed on Aug. 8, 2018, the entire disclosure of which is incorporated herein by reference.

TECHNICAL FIELD

The present invention is directed to a sustained-release pharmaceutical composition comprising an antipsychotic drug with a high drug to lipid ratio and a high encapsulation efficiency using at least one trapping agent. The high drug to lipid ratio, high encapsulation efficiency and sustained release profile of the pharmaceutical composition reduces the frequency of drug administration, increases patient compliance and improves the therapeutic outcome.

BACKGROUND

Schizophrenia and bipolar disorder are complex mental health diseases with debilitating symptoms. Aripiprazole, olanzapine, quetiapine, and risperidone are antipsychotic drugs approved for the treatment of schizophrenia and bipolar disorder. These medications can be administered orally in tablet, capsule or solution form, via injection, or by transdermal patch. However, patient compliance remains low for once-daily or twice-daily dosing regimens as patients with schizophrenic or bipolar disorder often forget to or actively resist taking the medicine. Therefore, it's difficult to ensure patient medication adherence to maintain the circulating drug concentration within the therapeutic window. Poor patient compliance increases the risk of relapse (Ther Adv Psychopharmacol. 2014; 4(5):198-219). In addition, it is costly to retain a healthcare professional or a care giver to administer the drug, even for once daily administration.

Liposomes have been widely used for developing sustained-release formulations for various drugs. Drug loading into liposomes can be attained either passively (the drug is encapsulated during liposome formation) or remotely/actively (creating a transmembrane pH- or ion-gradient during liposome formation and then the drug is loaded by the driving force generated from the gradients after liposome formation) (U.S. Pat. Nos. 5,192,549 and 5,939,096). Although the general methods of drug loading into liposomes are well documented in the literature, only a handful of therapeutic agents were successfully loaded into liposomes with high drug to lipid ratio or high drug encapsulation efficiency, which are important to sustain the release of the encapsulated therapeutic agent. Various factors can affect the encapsulation efficiency of liposomes, including but not limited to, the physical and chemical properties of the therapeutic agent, for example, hydrophilic/hydrophobic characteristics, dissociation constant, solubility and partition coefficient, lipid composition, trapping agent, reaction solvent, and particle size (Proc Natl Acad Sci USA. 2014; 111(6): 2283-2288 and Drug Metab Dispos. 2015; 43 (8): 1236-45).

Several liposomal formulations of olanzapine, quetiapine, and risperidone have been described in the literature. Babu et al. discloses a liposomal olanzapine formulation wherein the liposomes were 63.5 nm in diameter, with an encapsulation efficiency of around 60% and a final drug to lipid ratio (D/L) of 0.36. The in vitro release studies showed that about half of the liposome-encapsulated drug was released after 12 hours incubation at 37° C. (Indian J Res Pharm. Biotechnol. 2015; 3(2):151-156). Upadhyay et al. formulated liposomal dispersions of quetiapine fumarate with egg phosphatidylcholine and cholesterol (Drug Deliv. 2016; 23(4):1214-1221). This liposome was 152.2 nm in diameter, with an encapsulation efficiency of 79% and a final drug to lipid ratio (D/L) of 0.39 (Drug Deliv. 2016; 23(4):1214-1221). Nayak et al. prepared risperidone liposomes using soya phosphatidylcholine, cholesterol and DSPE-PEG2000. The liposomes were ~100 nm in diameter, had an encapsulation efficiency of about 50% and a final D/L of 0.05 for nasal administration (Clin Exp Pharmacol. 2015; 5:4). Imam et al. generated formulations incorporating risperidone in proniosomes using Phospholipon 90G, Span 60, and cholesterol, for transdermal drug delivery (Drug Deliv. 2015; 22(8): 1059-1070). These risperidone proniosomes were ~500 nm in diameter, had an encapsulation efficiency of 90% and a final D/L of 0.29 (Drug Deliv. 2015; 22(8):1059-1070). However, these liposomal antipsychotic formulations do not exhibit significant sustained drug release behavior or high drug encapsulation in liposome simultaneously.

There remains an unmet need for a sustained release formulation with a high drug encapsulation efficiency and high D/L ratio to reduce dosing frequency for antipsychotic drugs to treat schizophrenia and/or bipolar disorder and to improve therapeutic outcomes. The present invention addresses this need and other needs.

SUMMARY OF THE INVENTION

In one embodiment, a sustained release pharmaceutical composition comprises (a) at least one liposome comprising a bilayer membrane; (b) a trapping agent; and (c) an antipsychotic drug, wherein the bilayer membrane comprises at least one lipid and the molar ratio of the antipsychotic drug to the lipid is equal to or higher than about 0.4 is provided.

According to another embodiment of the present invention, methods are provided for treating schizophrenia or bipolar disorder, comprising the steps of administering a pharmaceutical composition described herein to a subject in need thereof.

Also provided are the use of the pharmaceutical composition described herein in the manufacture of a medicament for therapeutic and/or prophylactic treatment of schizophrenia or bipolar disorder.

Further provided is a medicament for treating schizophrenia or bipolar disorder, comprising a therapeutically effective amount of the pharmaceutical composition described herein.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

A further understanding of the nature and advantages of the present invention may be realized by reference to the remaining portions of the specification and the drawings.

DETAILED DESCRIPTION OF THE INVENTION

Figure 1:
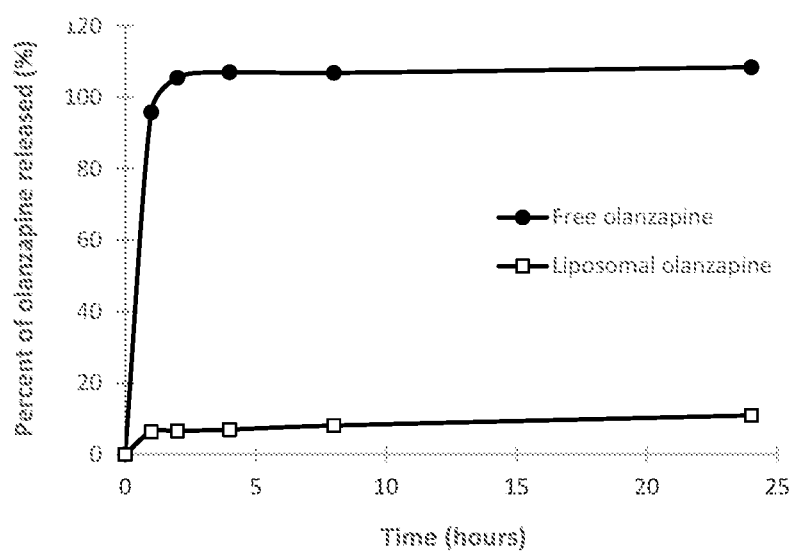
FIG. 1 is a line graph showing the in vitro release profiles of free olanzapine and liposomal olanzapine.

As employed above and throughout the disclosure, the following terms, unless otherwise herein, the singular forms "a," "an" and "the" include the plural reference unless the context clearly indicates otherwise.

All numbers herein may be understood as modified by "about." As used herein, the term "about" refers to a range of ±10% of a specified value.

An "effective amount," as used herein, refers to a dose of the pharmaceutical composition to reduce the symptoms and signs of schizophrenia or bipolar disorder, such as mania, delusions, hallucinations, and impairment of speech, behavior, and cognitive function, which is detectable clinically or brain atrophy, which is detectable radiologically through various imaging means. The term "effective amount" and "therapeutically effective amount" are used interchangeably.

The term "treating," "treated," or "treatment," as used herein, includes preventative (e.g. prophylactic), palliative, and curative methods, uses or results. The terms "treatment" or "treatments" can also refer to compositions or medicaments. Throughout this application, by treating is meant a method of reducing or delaying one or more symptoms or signs of schizophrenia or bipolar disorder or the complete amelioration of schizophrenia or bipolar disorder as detected by art-known techniques. Art recognized methods are available to detect schizophrenia and bipolar disorder and their symptoms. These include, but are not limited to, clinical examination, such as psychiatric evaluation, imaging or any possible blood-based biomarkers (for example, detection of low levels of brain-derived neurotrophic factor (BDNF) and γ-aminobutyric acid (GABA)), to name a few. For example, a disclosed method is considered to be a treatment if there is about a 1% reduction in one or more symptoms of schizophrenia and/or bipolar disorder in a subject when compared to the subject prior to treatment or control subjects. Thus, the reduction in one or more symptoms can be about 1, 5, 10, 20, 30, 40, 50, 60, 70, 80, 90, 100%, or any amount of reduction in between.

The term "schizophrenia," as used herein, encompasses a variety of types and subtypes of schizophrenia of various etiologies and causes, either known or unknown, including, but not limited to, anxiety/panic disorders, psychotic depression, and other psychotic and mental health disorders.

The term "bipolar disorder," as used herein, encompasses a variety of types and subtypes of bipolar disorder of various etiologies and causes, either known or unknown, including, but not limited to, bipolar I disorder, bipolar II disorder, cyclothymic disorder or drug or alcohol induced bipolar disorder.

The term "subject" can refer to a vertebrate having or at risk of developing schizophrenia or bipolar disorder or to a vertebrate deemed to be in need of treatment for schizophrenia or bipolar disorder. Subjects include all warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

Liposome

The terms "liposome," "liposomal" and related terms as used herein are characterized by an interior aqueous space sequestered from an outer medium by one or more bilayer membranes forming a vesicle. In certain embodiments, the interior aqueous space of the liposome is substantially free of a neutral lipid, such as triglyceride, non-aqueous phase (oil phase), water-oil emulsions or other mixtures containing non-aqueous phase. Non-limiting examples of liposomes include small unilamellar vesicles (SUV), large unilamellar vesicles (LUV), and multi-lamellar vesicles (MLV) with an average diameter ranges from 1-10 μm, 500-1000 nm, 50-500 nm, 50-450 nm, 50-400 nm, 50-350 nm, 50-300 nm, 50-250 nm, 50-200 nm, 100-500 nm, 100-450 nm, 100-400 nm, 100-350 nm, 100-300 nm, 100-250 nm or 100-200 nm.

Bilayer membranes of liposomes are typically formed by at least one lipid, i.e. amphiphilic molecules of synthetic or natural origin that comprise spatially separated hydrophobic and hydrophilic domains. Examples of lipid, including but not limited to, dialiphatic chain lipids, such as phospholipids, diglycerides, dialiphatic glycolipids, single lipids such as sphingomyelin and glycosphingolipid, and combinations thereof. Examples of phospholipid according to the present disclosure include, but not limited to, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1-palmitoyl-2-stearoyl-sn-glycero-3-phosphocholine (PSPC), 1-palmitoyl-2-oleoyl-sn-glycero-3-phosphatidylcholine (POPC), 1,2-distearoyl-sn-glycero-3-phosphocholine (DSPC), 1,2-dioleoyl-sn-glycero-3-phosphocholine (DOPC), hydrogenated soy phosphatidylcholine (HSPC), 1,2-dimyristoyl-sn-glycero-3-phospho-(1'-rac-glycerol) (sodium salt) (DMPG), 1,2-dipalmitoyl-sn-glycero-3-phospho-(1'-rac-glycerol) (sodium salt) (DPPG), 1-palmitoyl-2-stearoyl-sn-glycero-3-phospho-(1'-rac-glycerol) (sodium salt) (PSPG), 1,2-distearoyl-sn-glycero-3-phospho-(1'-rac-glycerol) (sodium salt) (DSPG), 1,2-dioleoyl-sn-glycero-3-phospho-(1'-rac-glycerol) (DOPG), 1,2-dimyristoyl-sn-glycero-3-phospho-L-serine (sodium salt) (DMPS), 1,2-dipalmitoyl-sn-glycero-3-phospho-L-serine (sodium salt) (DPPS), 1,2-distearoyl-sn-glycero-3-phospho-L-serine (sodium salt) (DSPS), 1,2-dioleoyl-sn-glycero-3-phospho-L-serine (DOPS), 1,2-dimyristoyl-sn-glycero-3-phosphate (sodium salt) (DMPA), 1,2-dipalmitoyl-sn-glycero-3-phosphate (sodium salt) (DPPA), 1,2-distearoyl-sn-glycero-3-phosphate (sodium salt) (DSPA), 1,2-dioleoyl-sn-glycero-3-phosphate (sodium salt) (DOPA), 1,2-dipalmitoyl-sn-glycero-3-phosphoethanolamine (DPPE), N-(carbonyl-methoxypolyethyleneglycol)-1,2-dipalmitoyl-sn-glycero-3-phosphoethanolamine (PEG-DPPE), 1-palmitoyl-2-oleoyl-sn-glycero-3-phosphoethanolamine (POPE), 1,2-distearoyl-sn-glycero-3-phosphoethanolamine (DSPE), N-(carbonyl-methoxypolyethyleneglycol)-1,2-distearoyl-sn-glycero-3-phosphoethanolamine (PEG-DSPE), 1,2-dioleoyl-snglycero-3-phosphoethanolamine (DOPE), 1,2-dipalmitoyl-sn-glycero-3-phospho-(1'-myo-inositol) (ammonium salt) (DPPI), 1,2-distearoyl-sn-glycero-3-phosphoinositol (ammonium salt) (DSPI), 1,2-dioleoyl-sn-glycero-3-phospho-(1'-myo-inositol) (ammonium salt) (DOPI), cardiolipin, L-α-phosphatidylcholine (EPC), and L-α-phosphatidylethanolamine (EPE). In some embodiments, the lipid is a lipid mixture of one or more of the foregoing lipids, or mixtures of one or more of the foregoing lipids with one or more other lipids not listed above, membrane stabilizers or antioxidants.

In some embodiments, the mole percent of the lipid in the bilayer membrane is about 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45 or any value or range of values therebetween (e.g., about 45-80%, about 45-75%, about 45-70%, about 45-65%, about 50-80%, about 50-75%, about 50-70%, or about 50-65%).

In some embodiments, the lipid comprises a mixture of a first lipid and a second lipid. In some embodiments, the first lipid is selected from the group consisting essentially of phosphatidylcholine (PC), HSPC, DSPC, DPPC, DMPC, PSPC and combination thereof and the second lipid is selected from the group consisting essentially of a phosphatidylethanolamine, phosphatidylglycerol, PEG-DSPE, DPPG and combination thereof. In other embodiments, the mole percent of the first lipid in the bilayer membrane is about 79.9, 79.5, 79.1, 78, 77, 76, 75, 74, 73, 72, 71,70, 69, 68, 67, 66, 65, 64, 63, 62, 61, 60, 59, 58, 57, 56, 55, 54, 53, 52, 51, 50, 49, 48, 47, 46, 45 or any value or range of values therebetween (e.g., about 45-79.9%, about 50-75%, about 50-70%, about 50-65%, about 45-75%, about 45-70% or about 45-6%5) and the mole percent of the second lipid in the bilayer membrane is about 20, 19, 18, 17, 16, 15, 14, 13, 12, 11, 10, 9, 8, 7, 6, 5, 4, 3, 2, 1, 0.9, 0.5, 0.1 or any value or range of values therebetween (e.g., about 0.1-20%, about 0.1-15%, about 0.1-10%, about 0.1-5%, about 0.1-4% or about 0.1-3%).

Bilayer membranes of liposomes further comprise less than about 55 mole percentage of steroids, preferably cholesterol. In certain embodiments, the mole % of steroid (such as cholesterol) in the bilayer membrane is about 20-55%, about 20-50%, about 20-45%, about 20-40%, about 25-55%, about 25-50%, about 25-45%, about 25-40%, about 30-55%, about 30-50%, about 30-45% or about 30-40%.

In one exemplary embodiment, the mole % of the lipid and cholesterol in the bilayer membrane is about 50-80%: 20-50% or about 45-80%: 20-55%. In another exemplary embodiment, the mole % of the first lipid, the second lipid and cholesterol in the bilayer membrane is about 45-79.9%: 0.1%-10%: 20-50%, about 45-79.5%: 0.5-10%: 20-50%, about 45-79.1%: 0.9-10%: 20-50%, about 45-79.9%: 0.1%-15%: 20-45%, about 45-79.5%: 0.5-15%: 20-45% or about 45-79.1%: 0.9-15%: 20-45% and the first lipid is HSPC, DMPC or DSPC and the second lipid is DSPE-PEG2000 or DPPG.

Remote Loading

The term "remote loading," as used herein, is a drug loading method which involves a procedure to transfer drugs from the external medium across the bilayer membrane of the liposome to the interior aqueous space by a polyatomic ion-gradient. Such gradient is generated by encapsulating at least one polyatomic ion as a trapping agent in the interior aqueous space of the liposome and replacing the outer medium of the liposome with an external medium, for example, pure water, sucrose solution and saline, with a lower polyatomic ion concentration by known techniques, such as column separation, dialysis or centrifugation. A polyatomic ion gradient is created between the interior aqueous space and the external medium of the liposomes to trap the therapeutic agent in the interior aqueous space of the liposomes. Exemplary polyatomic ion as trapping agents include, but are not limited to, sulfate, sulfite, phosphate, hydrogen phosphate, molybdate, carbonate and nitrate. Exemplary trapping agents include, but are not limited to, ammonium sulfate, ammonium phosphate, ammonium molybdate, ammonium sucrose octasulfate, triethylammonium sucrose octasulfate and dextran sulfate.

In an embodiment, the concentration of triethylammonium sucrose octasulfate is about 10 to 200 mM or about 50 to 150 mM. In another embodiment, the concentration of ammonium sulfate is about 100 to 600 mM, about 150 to 500 mM, about 200 to 400 mM or about 200 to 300 mM. In yet another embodiment, the concentration of ammonium phosphate is about 100 to 600 mM, about 150 to 500 mM or about 200 to 400 mM. In yet another embodiment, the concentration of dextran sulfate is about 0.1 to 10 mM, about 0.5 to 9 mM or about 1 to 8 mM.

In accordance with the invention, the liposome encapsulating a trapping agent can be prepared by any of the techniques now known or subsequently developed. For example, the MLV liposomes can be directly formed by a hydrated lipid film, spray-dried powder or lyophilized cake of selected lipid compositions with trapping agent; the SUV liposomes and LUV liposomes can be sized from MLV liposomes by sonication, homogenization, microfluidization or extrusion.

Pharmaceutical Compositions

The present invention is directed to a sustained release pharmaceutical composition, comprising (a) at least one liposome comprising a bilayer membrane; (b) a trapping agent; and (c) an antipsychotic drug, wherein the bilayer membrane comprises at least one lipid and the molar ratio of the drug to the lipid is above or equal to about 0.4.

In one embodiment, the sustained release pharmaceutical composition further comprises at least one pharmaceutically acceptable excipient, diluent, vehicle, carrier, medium for the active ingredient, a preservative, cryoprotectant or a combination thereof. In one exemplary embodiment, the weight percent of the bilayer membrane in the pharmaceutical composition is about 0.1-12%; the weight percent of the trapping agent in the pharmaceutical composition is about 0.1-10%; and the weight percent of the pharmaceutically acceptable excipient (such as sucrose, histidine, sodium chloride and ultrapure water), diluent, vehicle, carrier, medium for the active ingredient, a preservative, cryoprotectant or a combination thereof in the pharmaceutical composition is about 80.0-99.9%.

In certain embodiments, the therapeutic agent for treating schizophrenia or bipolar disorder is a typical or an atypical antipsychotic drug. Exemplary antipsychotic drug includes, but are not limited to, aripiprazole, olanzapine, quetiapine, risperidone, paliperidone, loxapine, and clozapine. The sustained release profile of the pharmaceutical composition prolongs the half-life and maintains the circulating concentration of the antipsychotic drug for a longer period of time, hence, sustains the therapeutic effect and reduces the frequency of drug administration.

In one aspect, the sustained release profile of the pharmaceutical composition is due to a high drug encapsulation efficiency. The % of the antipsychotic drug encapsulated in the liposome is above 50%, above 55%, above 60%, above 65%, above 70%, above 75%, or above 80%.

In another aspect, sustained release profile of the pharmaceutical composition is due to the higher drug to lipid molar ratio. In an exemplary embodiment, the molar ratio of the antipsychotic drug to the one or more lipids is above or equal to 0.4, 0.45, 0.5, 0.55, 0.6, 0.65, 0.7, 0.75, 0.8, 0.85, 0.9, 0.95 or 1.0, alternatively from about 0.4 to less than about 20, less than about 10, less than about 5, less than about 4, less than about 3, less than about 2 or less than about 1.

In yet another aspect, the half-life of the antipsychotic drug encapsulated in the pharmaceutical composition described herein is extended by at least 2-fold, at least 5-fold, at least 7.5-fold, at least 10-fold, or at least 20-fold compared to that of the free (non-encapsulated) antipsychotic drug.

The invention also provides methods of treating schizophrenia or bipolar disorder, comprising the administration of an effective amount of the pharmaceutical composition as described herein to a subject in need thereof, whereby the symptoms and/or signs of the schizophrenia or bipolar disorder in the subject are reduced.

The pharmaceutical composition is formulated to be suitable for cutaneous injection, such as subcutaneous, subdermal, intradermal, transdermal or intramuscular route. The pharmaceutical composition is also formulated to be administered as a transdermal patch.

The dosage of the pharmaceutical composition of the present invention can be determined by the skilled person in the art according to the embodiments. Unit doses or multiple dose forms are contemplated, each offering advantages in certain clinical settings. According to the present invention, the actual amount of the pharmaceutical composition to be administered can vary in accordance with the age, weight, condition of the subject to be treated, any existing medical conditions, and on the discretion of medical professionals.

In one embodiment, the pharmaceutical compositions disclosed herein display a significant sustained-release profile of the antipsychotic. For example, the pharmaceutical composition disclosed herein extended the half-life of subcutaneous administered risperidone to 65.8 hours in rats (as described in Example 6) compared to the half-life of either oral administered free risperidone (5.9 hours) or transdermal administered liposomal risperidone formulation (21.6 hours) reported in the literature (Drug Deliv. 2015; 22(8):1059-1070). These pharmaceutical compositions are developed to reduce the dosing frequency from twice-daily or daily to once every two days, once every three days, once every five days, weekly, once every two weeks, once a month, once every two months, once every three months, once every four months, once every five months or once every six months.

EXAMPLES

Embodiments of the present invention are illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the invention. During the studies described in the following examples, conventional procedures were followed, unless otherwise stated.

Example 1. Preparation of Liposomal Aripiprazole Formulation

Empty liposomes were prepared by a lipid film hydration-extrusion method. HSPC, cholesterol, and DSPE-PEG2000 (mole percent 59.5/39.6/0.9) were dissolved in chloroform and a thin lipid film was formed by removing the organic solvent under vacuum in a rotary evaporator. The dry lipid film was hydrated in 75 mM triethylammonium sucrose octasulfate (pH 6.0) at 60° C. for 30 min and liposomes were formed with triethylammonium sucrose octasulfate encapsulated in the aqueous core. After six freeze-thaw cycles between liquid nitrogen and water at 60° C., the liposomes were subsequently extruded ten times through polycarbonate filter membranes with a pore size of 0.2 µm. Unencapsulated triethylammonium sucrose octasulfate was removed by dialysis against a 9.4% sucrose solution.

A reaction mixture containing 1.0 mg/mL of aripiprazole (Abblis Chemicals LLC, USA), empty liposomes (with 2.5 mM of lipids), 100 mM citrate buffer (pH 5.0) and 5% (v/v) dimethyl sulfoxide prepared according to the preceding paragraph was incubated at 60° C. for 30 min. The unencapsulated aripiprazole was separated by a Sephadex™ G-50 Fine gel (GE Healthcare, USA) or dialysis bag (Spectrum Labs, USA) against a 9.4% sucrose solution to obtain liposomal aripiprazole formulation. Encapsulated aripiprazole concentrations and the lipid concentrations of liposomal aripiprazole formulation were measured using an ultraviolet/visible (UV/Vis) spectrophotometer to calculate the drug to lipid molar ratio (D/L) of the liposomal aripiprazole formulation.

The encapsulation efficiency was calculated by the drug to lipid molar ratio (D/L) of the liposomal aripiprazole formulation compared to the nominal D/L of reaction mixture, which was calculated by dividing the concentration of aripiprazole by the lipid concentration of the empty liposome.

Using 75 mM triethylammonium sucrose octasulfate as a trapping agent, the liposomal aripiprazole formulation has a final D/L of 0.81 and an encapsulation efficiency of 90.4%.

Example 2. Preparation of Liposomal Olanzapine Formulation

Empty liposomes were prepared according to Example 1. The bilayer membrane was comprised of HSPC, cholesterol, and DPPG (mole percent 59.5/39.6/0.9) and the trapping agent was 300 mM ammonium sulfate.

A reaction mixture containing 6.1 mg/mL of olanzapine (TCI America, US), 21.3 mM of lipids of empty liposomes, and 35 mM histidine buffer (pH 7.35) was incubated at 60° C. for 15 min, and then the unencapsulated olanzapine was separated by a Sephadex™ G-50 Fine gel (GE Healthcare) or dialysis bag (Spectrum Labs) against a 9.4% sucrose solution. The olanzapine (drug) concentrations and lipid concentrations of the reaction mixture and olanzapine encapsulated liposomes were measured using an ultraviolet/visible (UV/Vis) spectrophotometer. The D/L and encapsulation efficiency of liposomal olanzapine formulation were calculated according to Example 1. The particle size distribution was measured by a dynamic light scattering instrument (Zetasizer Nano-ZS90, Malvern).

Using 300 mM ammonium sulfate as a trapping agent, the liposome formulation has a final D/L of 0.56 and an encapsulation efficiency of 61.4%. The mean diameter of the liposomes was 198.8 nm.

Example 3. Preparation of Liposomal Risperidone Formulation

Empty liposomes were prepared according to Example 1. The bilayer membrane was comprised of HSPC, cholesterol, and DSPE-PEG2000 (mole percent 59.5/39.6/0.9) and the trapping agent was 300 mM ammonium sulfate.

A reaction mixture containing 5.4 mg/mL of risperidone (TCI America, US), 24.4 mM of lipids of empty liposomes, and 20 mM histidine buffer (pH 6.5) was incubated at 60° C. for 15 min and then the unencapsulated risperidone was separated by a Sephadex™ G-50 Fine gel (GE Healthcare) or dialysis bag (Spectrum Labs) against a 9.4% sucrose solution. Risperidone (drug) concentrations and lipid concentrations of the reaction mixture and risperidone encapsulated liposomes were measured using an ultraviolet/visible (UV/Vis) spectrophotometer. The D/L and encapsulation efficiency of liposomal risperidone formulation were calculated according to Example 1.

Using 300 mM ammonium sulfate as a trapping agent, the liposome formulation has a final D/L of 0.44 and an encapsulation efficiency of 80.2%.

Example 4. The Effect of Different Trapping Agents on Drug Loading Profile

The liposome formulations were prepared according to Example 1, with the following trapping agents: (1) 75 mM of triethylammonium sucrose octasulfate, (2) 250 mM of ammonium sulfate, (3) 300 mM of ammonium sulfate, and (4) 7 mM of dextran sulfate. Table 1 shows the effect of different trapping agents on drug loading.

TABLE 1

The drug loading profile of different trapping agents

| Bilayer Membranes (mole percent) | Compound | Trapping Agent | Purified D/L (mole/mole) | Encapsulation Efficiency (%) | Average Particle Size (nm) |
|---|---|---|---|---|---|
| HSPC/cholesterol/DSPE-PEG2000 (59.5/39.6/0.9) | Aripiprazole | 1 | 0.81 | 90.4 | n.d. |
| HSPC/cholesterol (60/40) | Aripiprazole | 1 | 0.70 | 78.5 | 203.9 |
| HSPC/cholesterol/DSPE-PEG2000 (59.5/39.6/0.9) | Paliperidone | 1 | 0.42 | 90.1 | n.d. |
| HSPC/cholesterol/DSPE-PEG2000 (59.5/39.6/0.9) | Clozapine | 1 | 0.56 | 92.1 | n.d. |
| HSPC/cholesterol/DSPE-PEG2000 (59.5/39.6/0.9) | Olanzapine | 1 | 0.45 | 93.7 | n.d. |
| HSPC/cholesterol/DSPE-PEG2000 (58.3/38.8/2.9) | Olanzapine | 2 | 0.47 | 97.0 | n.d. |
| DMPC/cholesterol/DSPE-PEG2000 (59.5/40/0.5) | Olanzapine | 3 | 0.61 | 67.6 | 173.3 |
| HSPC/cholesterol/DPPG (59.5/39.6/0.9) | Olanzapine | 3 | 0.56 | 61.4 | 198.8 |
| DSPC/cholesterol/DSPE-PEG2000 (59.5/39.6/0.9) | Quetiapine fumarate | 4 | 0.53 | 94.8 | 925.3 |
| HSPC/cholesterol/DSPE-PEG2000 (59.5/39.6/0.9) | Risperidone | 1 | 0.80 | 82.0 | n.d. |
| HSPC/cholesterol/DSPE-PEG2000 (59.5/39.6/0.9) | Risperidone | 3 | 0.99 | 95.3 | n.d. |
| HSPC/cholesterol/DPPG (59.5/39.6/0.9) | Risperidone | 3 | 0.68 | 78.0 | 205.6 | n.d., not determined.

Example 5. Prolonged Release Profile of Liposomal Olanzapine

To setup an in vitro release system, 1.0 mL of liposomal olanzapine formulation, prepared according to Example 2, and 1.0 mL of free olanzapine were each put in individual dialysis bags (Spectra/Pro®6 dialysis membrane, MWCO 50 kDa, Spectrum Labs), with both ends of the dialysis bags being sealed. Each dialysis bag was then immersed in 20 mL PBS at pH 7.4 in a 50-mL centrifuge tube and incubated at 37±1° C. water bath. At designated time points after incubation (1, 2, 4, 8, and 24 hours), 1 mL aliquot from 20-mL PBS was sampled and 1 mL of fresh PBS was added to refill the sampling place each time. Drug concentrations of the sampled aliquots at each time point were determined through UV/Vis absorbance measurements of the sampled aliquots to create the in vitro release profile.

As demonstrated in FIG. 1, almost a hundred percent of olanzapine was released through the dialysis bag within 2 hours in the free olanzapine group. In contrast, the releasing rate of olanzapine from the liposomal olanzapine formulation through the dialysis bag was about 10% and extended over 24 hours, which was significantly lower than that of the free olanzapine (>99%). The slow release profile of liposomal olanzapine formulation demonstrates the liposome formulation of the present invention sustained the release of olanzapine.

Example 6. Pharmacokinetics (PK) Study of Liposomal Risperidone

An in vivo PK evaluation of the liposomal risperidone formulation was performed using Jugular vein cannulated (JVC) female Sprague-Dawley rats. The rats were housed in a holding room which operated on a 12-hr light/12-hr dark circadian cycle with free access to water and food.

The rats were divided into two groups (n=3 in each group), one group received subcutaneous injection of 10 mg/kg of free risperidone, prepared by dissolving risperidone in ultrapure water, containing 25 mN HCl, with a final concentration of 5 mg/mL of risperidone. The other group received subcutaneous injection of 10 mg/kg of liposomal risperidone, prepared according to Example 3. Blood samples were collected at 15 min, 1, 2, 4, 8, 24, 48, 72, 96, and 168 hours post-injection. Plasma samples were obtained by centrifugation, kept frozen at −80° C. and analyzed using a noncompartmental analysis model in PKSolver (Comput Methods Programs Biomed. 2010; 99(3):306-314). The PK parameters of the two risperidone formulations are summarized in Table 2.

The results in Table 2 show the $C_{max}$ of liposomal risperidone group was 15% of that of free risperidone group, the half-life ($t_{1/2}$) of liposomal risperidone was significantly longer compared to that of the free risperidone group, and the area under the curve ($AUC_{0-t}$) indicates 33.9% of risperidone was released from liposomes after 168 hours post-injection compared to the $AUC_{0-t}$ of free risperidone, which indicates 100% drug was released after 8 hours post-injection.

TABLE 2

PK parameters derived from rats after single subcutaneous injection of liposomal risperidone and free risperidone

| Parameters | Unit | Free Risperidone | Liposomal Risperidone |
| --- | --- | --- | --- |
| $t_{1/2}$ | h | 1.09 | 65.8 |
| $C_{max}$ | ng/mL | 4,510.0 | 677.3 |
| $AUC_{0-t}$ | h × ng/mL | 13,245.1 | 4,490.5 |
| $AUC_{0-inf}$ | h × ng/mL | 13,330.4 | 4,936.0 |

Figure 2:
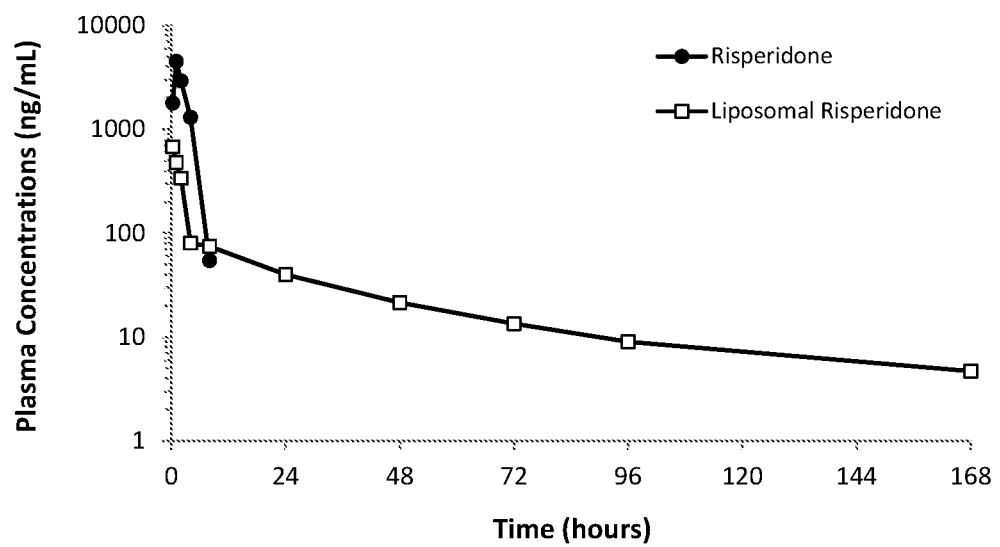
FIG. 2 is a line graph showing the plasma risperidone concentration in rats after subcutaneous injection of free risperidone and liposomal risperidone.

In addition, FIG. 2 shows risperidone was undetectable in the plasma of rats receiving free risperidone injection between 8 and 24 hours post injection whereas risperidone was detected in the plasma of rats receiving liposomal risperidone up to 168 hours post injection. The results support a conclusion that the claimed pharmaceutical composition sustained the release of risperidone.

The invention claimed is:

1. A pharmaceutical composition, comprising
  (a) at least one liposome comprising a bilayer membrane, said bilayer membrane comprises about 45 to about 79.9 mole % of a first lipid that is a phosphatidylcholine (PC), 1,2-distearoyl-sn-glycero-3-phosphocholine (HSPC), 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), 1-palmitoyl-2-stearoyl-sn-glycero-3-phosphocholine (PSPC) or any combination thereof, about 20 to about 55% mole % of cholesterol and optionally 0.1-20% mole % of a second lipid that is phosphatidylethanolamine, phosphatidylglycerol, N-(carbonyl-methoxypolyethyleneglycol)-1,2-distearoyl-sn-glycero-3-phosphoethanolamine (PEG-DSPE), 1,2-dipalmitoyl-sn-glycero-3-phospho-(1'-rac-glycerol) (DPPG) or any combination thereof;
  (b) a trapping agent that is triethylammonium sucrose octasulfate, ammonium sulfate, dextran sulfate, or any combination thereof; and
  (c) an antipsychotic drug that is aripiprazole, olanzapine, quetiapine, risperidone, clozapine, or any combination thereof,
  wherein when the antipsychotic drug is aripiprazole or clozapine, the trapping agent is triethylammonium sucrose octasulfate, when the antipsychotic drug is olanzapine, the trapping agent is ammonium sulfate; when the antipsychotic drug is quetiapine, the trapping agent is dextran sulfate and when the antipsychotic drug is risperidone, the trapping agent is triethylammonium sucrose octasulfate or ammonium sulfate;
  wherein the molar ratio of the drug to the lipid is equal to or higher than 0.47 and the antipsychotic drug is encapsulated in the liposome with an encapsulation efficiency higher than 60%.

2. The pharmaceutical composition of claim 1, wherein the mean particle size of the liposomes is from about 50 nm to 10 μm.

3. The pharmaceutical composition of claim 1, wherein the concentration of triethylammonium sucrose octasulfate is about 10 to 200 mM.

4. The pharmaceutical composition of claim 1, wherein the concentration of ammonium sulfate is about 100 to 600 mM.

5. The pharmaceutical composition of claim 1, wherein the concentration of dextran sulfate is about 0.1 to 10 mM.

6. A method of treating schizophrenia or bipolar disorder, comprising: administering the pharmaceutical composition of claim 1 to a subject in need thereof.

7. The method of claim 6, wherein the half-life of the antipsychotic drug is extended by at least 2-fold, at least 5-fold, at least 7.5-fold, at least 10-fold, or at least 20-fold compared to that of the free antipsychotic drug.

8. The method of claim 6, wherein the pharmaceutical composition is administered at least once every three days, at least once every week, at least once every two weeks or at least once a month.

9. The method of claim 6, wherein the pharmaceutical composition is administered by cutaneous injection.

10. The method of claim 9, wherein the cutaneous injection includes subcutaneous, subdermal, intradermal, transdermal or intramuscular route.

11. The pharmaceutical composition of claim 1, wherein the first lipid is HSPC and second lipid is PEG-DSPE, DPPG or the combination thereof.

12. The pharmaceutical composition of claim 1, wherein the first lipid is DMPC and the second lipid is PEG-DSPE.

13. The pharmaceutical composition of claim 1, wherein the first lipid is DSPC and the second lipid is PEG-DSPE.

14. The pharmaceutical composition of claim 1, wherein the first lipid is HSPC, DMPC, DSPC or any combination thereof, the second lipid is PEG-DSPE, DPPG or any combination thereof,
  wherein when the antipsychotic drug is aripiprazole or clozapine, the trapping agent is triethylammonium sucrose octasulfate, when the antipsychotic drug is olanzapine, the trapping agent is ammonium sulfate; when the antipsychotic drug is quetiapine, the trapping agent is dextran sulfate and when the antipsychotic drug is risperidone, the trapping agent is triethylammonium sucrose octasulfate or ammonium sulfate; and
  wherein the molar ratio of the drug to the lipid is equal to or higher than 0.47 and the antipsychotic drug is encapsulated in the liposome with an encapsulation efficiency higher than 60%.

* * * * *